United States Patent [19]

Chuang et al.

[11] Patent Number: 4,954,336
[45] Date of Patent: Sep. 4, 1990

[54] NON-AEROSOL PUMP HAIR SPRAY COMPOSITIONS

[75] Inventors: Jui-Chang Chuang, Wayne; Edward Walls, Jr., Cranford; Stephen C. Johnson, Newton; Mohammed Tazi, Wayne, all of N.J.

[73] Assignee: GAF Chemicals Corporation, Wayne, N.J.

[21] Appl. No.: 354,870

[22] Filed: May 22, 1989

[51] Int. Cl.$^5$ ................................................. A61K 7/11
[52] U.S. Cl. ......................................... 424/71; 424/78; 424/DIG. 2
[58] Field of Search ...................... 424/71, 78, DIG. 2

[56] References Cited

U.S. PATENT DOCUMENTS 3,862,306  1/1975  Block et al. ........................... 424/47
3,922,341  11/1975 Abegg et al. .......................... 424/47
4,036,241  7/1977  Karg et al. ............................. 132/7
4,079,042  3/1978  Topfl et al. ........................ 260/63 R Primary Examiner—Merrell C. Cashion, Jr.
Assistant Examiner—Amy Hulina
Attorney, Agent, or Firm—Walter Katz; Marilyn J. Maue; Joshua J. Ward

[57] ABSTRACT

Non-aerosol pump hair spray compositions herein are applied as a fine spray mist, without nozzle clogging, and dried rapidly, to provide superior hair holding power. The compositions includes a hair fixative resin which is a copolymer of maleic anhydride and an alkyl vinyl ether, and the ethyl and butyl half-esters thereof, in an amount of between 6 and 20% solids. In suitable embodiments of the invention, the resin is the $C_2$–$C_4$ alkyl half-ester of maleic anhydride and $C_1$–$C_5$ alkyl vinyl ether having a relative viscosity of about 1.20 to 1.35 (1% in ethanol).

9 Claims, No Drawings

NON-AEROSOL PUMP HAIR SPRAY COMPOSITIONS

BACKGROUND OF THE INVENTION

1. Field of the Invention

This invention relates to a non-aerosol pump hair spray composition which can be applied as a fine spray mist, which dries rapidly, and which provides superior hair holding power, without nozzle clogging.

2. Description of the Prior Art

Aerosol hair spray products contain a hair spray composition which includes a hair fixative resin and a volatile propellant. These cosmetic products apply the resin as a fine, dispersed spray which exhibits excellent hair holding power. However, the propellants used therein are believed to adversely affect the ozone layer of the atmosphere. For this reason, it is desired to provide non-aerosol, pump hair spray compositions which exhibit the same advantageous properties as aerosol hair sprays.

Non-aerosol hair spray compositions are applied by means of a pressure actuated pump nozzle. However, commercially available pumps for non-aerosol application have restricted nozzle orifices which limits its use to resin compositions having a low solids content. Unfortunately, the restriction on resin solids content reduces the holding power of the hair spray. Furthermore, if the solids content of the resin composition is increased, the spray pattern becomes streamed rather than sprayed. This effect is caused by the inability of the nozzle to effectively break up hair spray compositions of high solids content. Furthermore, nozzle clogging becomes evident if the solids content is increased. Accordingly, hair spray resins used in present non-aerosol hair spray products generally are present at about a 5% solids level, which enables only relatively weak hair holding power and poor curl retention.

Accordingly, it is an object of this invention to provide a non-aerosol pump hair spray composition and cosmetic product which can be applied to the user as a fine spray mist, which dries rapidly, and which has superior hair holding power, without nozzle clogging.

A particular object herein is to provide a hair spray composition having a high solids content hair fixative resin which can be applied through a nozzle pump as a fine mist and which exhibits excellent hair holding power.

SUMMARY OF THE INVENTION

What is described herein is a non-aerosol hair spray composition capable of being applied by the user as a fine spray mist which dries rapidly and provides effective hair holding power without nozzle clogging. The composition includes from about 6 to 20% of a hair fixative resin which is a copolymer of maleic anhydride and an alkyl vinyl ether, and the $C_2$–$C_4$ alkyl half-ester, e.g. the ethyl and butyl half-esters thereof, in ethanol at about 50% solids. In one embodiment of the invention, the ethyl half-ester of maleic anhydride and methyl vinyl ether copolymer having a relative viscosity of about 1.20–1.35, at 8–14% solids, is used in hair spray formulations, the carboxyl groups of which are 10 to 100% neutralized with a water soluble base, and about 65 to 94% of ethanol solvent is included.

DETAILED DESCRIPTION OF THE INVENTION

In accordance with the present invention, the resins utilized in the non-aerosol pump hair spray compositions are copolymer resins of maleic anhydride and an alkyl vinyl ether, prepared within a desired viscosity range.

These resins may be prepared by a conventional solution polymerization process which provides the anhydride copolymer and its half-ester resin within the requisite low viscosity range. Additionally, these resins can also be prepared by a solution feed, solution polymerization process. The latter process is characterized by precharging an alkyl vinyl ether, preferably in a solvent, into a reactor, and feeding therein a solution of maleic anhydride in a selected organic solvent. Preferred solvents for the maleic anhydride reactant is selected from functional organic solvents, such as ketones, esters and ethers. Acetone, ethyl acetate and tetrahydrofuran are most preferred. Reaction is effected in the presence of a suitable free radical initiator.

The process of preparing suitable resins for use herein will be illustrated hereinafter by maleic anhydride-acetone solutions. At 25° C., approximately 227 g. of maleic anhydride can be dissolved in 100 g. of acetone. The solution of maleic anhydride (MA) in acetone promotes a homogeneous reaction system characterized by a large diffusion distance between polymeric molecules. Preferably, the MA: acetone weight ratio in the feed solution is about 1:1 to 1:2, and, most preferably, about 1:1.5.

The MA-acetone solution is fed into a reactor precharged with $C_1$–$C_5$ vinyl ether, e.g. methyl vinyl ether, alone, or preferably in a small amount of the solvent. The precharged ether solution generally contains only a 10% or less molar excess of the ether compound over the stoichiometric amount required for copolymerization with MA to produce the 1:1 alternating MA-MVE copolymer.

The solvent is present in the system in an amount sufficient to keep both reactants and copolymer products in solution during the polymerization. The solvent also facilitates formation of the requisite low viscosity copolymers.

The free radical initiator for the polymerization reaction can be any known initiator to effect polymerization between MA and MVE, e.g. peroxy esters, acyl peroxides, alkyl peroxides, and the like. Preferably, however, the free radical initiator in this process is a peroxy ester, e.g. t-amylperoxy pivalate (TAPP) (Lupersol 554 M75-Pennwalt Corp.). The TAPP initiator is a liquid which will undergo decomposition to leave acetone as a by-product which is easily separated from the copolymer reaction product.

The free radical initiator can be introduced into the reactor in one shot, but preferably, it is admitted in increments, and most preferably, while feeding the MA solution into the reactor. The initiator solution suitably comprises about 1–10%, preferably about 4% by wt., based on the amount of MA present.

The precharged reactor is maintained at a temperature of about 55°–85° C., and, preferably, at about 75° C., while both the initiator and the MA feed solution is introduced. Preferably, the MA solution is fed slowly into the reactor during an extended period of time.

After introduction of the initiator and MA solution into the reactor prechargedwith MVE in acetone, the reaction solution is held at about 75° C. for 1 hour to complete the solution polymerization of the monomers.

The reactor then is cooled to about 25°–30° C., and excess MVE is removed. The remaining acetone solution containing the copolymer reaction product then is discharged from the reactor.

The reaction product is the copolymer of MA and MVE in acetone solution. The relative viscosities of the anhydride copolymers obtained are below 1.3, as determined by measurement in 2-butanone (1% solution).

Solution polymerization provides a substantially quantitative yield of the anhydride copolymer in the form of a clear solution. The solids content of the product is generally at least 35%, and usually is 50%, or more.

If desired, the acetone can be separated from the copolymer by distillation, stripping, or by addition of a non-solvent for the copolymer. However, it is convenient to half-esterify the copolymer solution directly with an alkanol, e.g. ethanol or butanol, to form the half-ester of MA-MVE copolymer in ethanol. The acetone then can be removed readily from the higher boiling alkanol. The half-ester copolymer in ethanol has a relative viscosity of about 1.20 to 1.35, and a solids content of about 50%.

The copolymeric resins thus prepared by the above described solution feed, solution polymerization process have the requisite viscosity range for use as the active ingredient in a non-aerosol pump hair spray formulation. The resins are employed in concentrations between about 6 to 20% solids, preferably 8 to 14% solids. Such cosmetic products can be used over an extended period of time to generate fine spray mists without experiencing any nozzle clogging.

The hair treatment formulations herein include a solvent for the resin, such as a lower alcohol, e.g. ethanol, an aqueous ethanol solution, isopropanol and the like, etc. Generally aqueous ethanol is preferred and in an amount of about 65 to 94% of the formulation.

In preparing the hair treatment formulations, the copolymers are about 5–100% neutralized with a water soluble base to provide water solubility and shampoo removability, and preferably, about 10% neutralized. Examples of suitable water-soluble bases include ammonium hydroxide, sodium hydroxide, potassium hydroxide; mono-, di-, and tripropanolamine, dimethyl- stearamine, aminomethylpropanol, aminomethylpropanediol, or mixtures thereof. Water-soluble organic bases are preferred and aminomethylpropanol is especially preferred.

Improved results are obtained when plasticizer for the polymer is added to the formulation. When used, about 0.05 to 0.5 percent by weight, based on the weight of the copolymer, of either an ester or silicone plasticizer is added. Suitable ester plasticizers include isocetyl stearate, diisopropyl adipate, isohexyl laurate, isohexyl palmitate, and isocetyl stearate. Isocetyl stearate is preferred. Suitable silicones include dimethicone copolyol (Silicone Fluid SF-1066, General Electric Co.) which is the reaction product of dimethyl siloxane and ethylene oxide, propylene oxide and/or glycols. Some degree of plasticization is achieved by the water present in the compositions of the invention.

The formulations are charged into a suitable container and fitted with a pump valve. When operated through a pressure release nozzle, the formulations provide a fine spray mist and avoids nozzle clogging when the resins are employed within the predetermined relative viscosity range and solids content defined above.

Having thus generally described the invention, reference is now had to the following examples which provide specific and preferred embodiments but which are not to be construed as limiting to the scope of the invention as more broadly described above and in the appended claims. All parts given are by weight unless otherwise indicated.

EXAMPLE 1

PREPARATION OF MALEIC ANHYDRIDE (MA) - METHYL VINYL ETHER (MVE) BY SOLUTION FEED, SOLUTION POLYMERIZATION

In a 1-liter pressure reactor:
1. Dissolve 98 g. of MA into 147 g. of acetone (1:1.5 solution);
2. Charge the freshly prepared solution into a syringe pump;
3. Charge 143 g. of acetone into the reactor;
4. Charge 63.8 g. of MVE into the reactor (10% mole excess MVE);
5. Heat the reactor until the temperature of the charge reaches 70° C.;
6. When the temperature stabilizes at 70° C., take this as time 0; at time 0:

|  |  |  |
|---|---|---|
|  | (a) | Introduce the initiator, e.g. 3.92 g. of t-amylperoxy pivalate, (4% based on MA) in 20 ml of the MA solution in one shot; |
|  | (b) | Continuously feed the rest of the MA solution over a 4-hour period; |
| at time 240 min. | (c) | Hold the reaction mixture at 70° C. for 1 hour; |
| at time 300 min. | (d) | Cool the reactor to 25–30° C.; remove excess MVE and collect it; and |
|  | (e) | Discharge the reaction product as a solution. |

The anhydride form of the MA-MVE copolymer in acetone is present in quantitative amount as a clear solution having a solids content of 35% and a relative viscosity of 1.25 (measured as a 1% solution in 2-butanone).

EXAMPLE 2

PREPARATION OF MALEIC ANHYDRIDE (MA) -METHYL VINYL ETHER (MVE) COPOLYMER BY SOLUTION POLYMERIZATION

A 1-liter pressure reactor was charged with 264.00 g. of dry acetone and 41.76 g. of methyl vinyl ether (0.72 mole). The reactor was heated to 78° C. by steam in the reactor jacket. Immediately thereafter 1.18 g. of decanoyl peroxide initiator in 9.0 g. of acetone was added into the reactor, 58.80 g. of maleic anhydride (0.60 mole) was fed into the reactor over a period of 4 hours while holding the reactor temperature at 85° C. An hour later a second initiator solution of 1.18 g. of decanoyl peroxide in 9.0 g. of acetone was fed into the reactor over a 3-hour period. The reactor then was charged with 27.84 g. of methyl vinyl ether (0.48 mole). A second maleic anhydride (39.20 g., 0.40 mole) and a third initiator solution (0.5 g. of decanoyl peroxide in 7.0 g. of acetone) was charged simultaneously over a period of 2 hours. The reactor contents then were mixed for another 30 minutes. Testing by triphenylphosphine paper showed no residual maleic anhydride monomer. The maleic anhydride-methyl vinyl ether copolymer then was cooled to 40° C. and discharged. The anhydride copolymer thus obtained was a clear solution having a solids content of 35% and a relative viscosity of 1.26 (measured as a 1% 2-butanone solution).

EXAMPLE 3

The anhydride copolymers of Examples 1 and 2 were esterified with ethanol by solvent interchange with removal of acetone to provide the ethyl half-ester of MA-MVE copolymer in ethanol at 50% solids having relative viscosities of 1.26 and 1.27, respectively.

EXAMPLE 4

This example provides representative formulations for a non-aerosol hair spray according to the invention. The half-ester of Example 2 was dissolved in 95% ethanol and 10% neutralized with 2-amino-2-methyl-1-propanol (AMP).

|  | Formulations | |
|---|---|---|
|  | A Wt. (g) | B Wt. (g) |
| Copolymer of Ex. 2 (as ethyl half-ester) (50% solids) | 20.00 | 24.00 |
| Ethanol (95%) | 79.56 | 79.47 |
| AMP | 0.44 | 0.53 |

The above formulations were charged into a plastic container fitted with a Mistette II (Calmar) valve and sprayed on clean, virgin tresses. The spray patterns developed were fine dispersed mists which dried to non-tacky, clear, transparent film within about 8–12 seconds. Formulation A exhibited a curl retention of 88% after 30 minutes, 85% after 40 minutes, 58% after 60 minutes, and 50% after 80 minutes. Formulation B had corresponding curl retention values of 88%, 85%, 78% and 65%. Similar formulations with the commercial ethyl half-ester of MA-MVE copolymer, e.g. Gantrez® ES-225 (GAF) having a relative viscosity of 1.45–1.55, permitted only a 5% solids level, which provided corresponding curl retention percentages of only 58%, 50%, 38% and 35%.

What is claimed is:

1. A non-aerosol pump hair spray composition capable of being applied by the user as a fine spray mist which dries rapidly and provides effective hair holding power without nozzle clogging consisting essentially of from about 6 to 20% by weight of a hair fixative resin derived from an ethanol solution of a $C_2$–$C_4$ alkyl which half-ester of a 1:1 alternating copolymer of maleic anhydride and a $C_1$–$C_5$ alkyl vinyl ether, the solution having a relative viscosity of about 1.20 to about 1.35, the carboxyl groups of which are 10 to 100% neutralized with a water soluble base and about 65 to 94% ethanol or aqueous ethanol solvent.

2. A non-aerosol pump hair spray composition according to claim 1 comprising about 8–14% by weight of said resin.

3. A non-aerosol pump hair spray according to claim 1 in which the alkyl half-ester resin is the ethyl half-ester.

4. A non-aerosol pump hair spray composition according to claim 1 in which the alkyl half-ester resin is the butyl half-ester.

5. A non-aerosol pump hair spray composition according to claim 1 additionally including about 0.05 to 0.5% by weight, based upon the copolymer, of a plasticizer selected from a fatty acid ester or a silicone.

6. A non-aerosol pump hair spray composition according to claim 1 wherein said base is a water soluble organic base.

7. A non-aerosol pump hair spray composition according to claim 6 wherein said organic base is an organic amine.

8. A non-aerosol pump hair spray composition according to claim 7 wherein said organic amine is 2-amino-2-methyl-1-propanol or dimethylstearamine.

9. A non-aerosol pump hair spray composition according to claim 1 wherein said solvent is aqueous ethanol.

* * * * *